United States Patent
Boomgaarden (10) Patent No.: US 6,402,374 B1
(45) Date of Patent: Jun. 11, 2002

(54) METHOD AND SYSTEM FOR DETERMINING A SOURCE-TO-IMAGE DISTANCE IN A DIGITAL RADIOGRAPHIC IMAGING SYSTEM

(75) Inventor: Jonathan C. Boomgaarden, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 33 days.

(21) Appl. No.: 09/747,541

(22) Filed: Dec. 22, 2000

(51) Int. Cl.⁷ .............................................. G01D 18/00
(52) U.S. Cl. .................................................... 378/207
(58) Field of Search .................................. 378/207, 165

(56) References Cited

U.S. PATENT DOCUMENTS 4,766,603 A * 8/1988 Okabe et al. ............... 378/152
5,224,145 A * 6/1993 Gunji ......................... 378/150

* cited by examiner

Primary Examiner—Robert H. Kim
Assistant Examiner—Allen C. Ho
(74) Attorney, Agent, or Firm—Fletcher, Yoder & Van Someren (57) ABSTRACT

The present technique provides a method for calculating the source-to-image distance of an imaging system utilizing the intensity of the x-ray. The present technique involves measuring the source-to-image distance using the x-ray intensity and the inverse square relationship between the intensity and the distance. The present technique can be implemented with a digital detector system using fixed timing, relying on the measuring capability of the digital detector to determine intensity, or it can be implemented using a phototiming approach, using either a digital detector or a conventional ion chamber to measure total exposure.

24 Claims, 4 Drawing Sheets

METHOD AND SYSTEM FOR DETERMINING A SOURCE-TO-IMAGE DISTANCE IN A DIGITAL RADIOGRAPHIC IMAGING SYSTEM

FIELD OF THE INVENTION

The present invention relates generally to digital imaging systems and, more particularly, to a calibration and setup procedure for determining a separation distance between a source and a digital detector in an imaging system.

BACKGROUND OF THE INVENTION

The installation and setup procedures for digital imaging systems can be complex and time-consuming. To comply with customer requirements and various regulatory and safety standards, such procedures generally require the determination of a variety of factors, including the accurate positioning of a x-ray source with respect to a x-ray detector. For example, the determination and establishment of fixed setpoints (or detent positions) for setting the separation distance between the x-ray source and x-ray detector and calibrating the system such that an accurate readout of the separation distance can be obtained are typical setup procedures. The determination and establishment of this separation distance, referred to as the source-to-image distance (SID), assists in appropriately controlling the size of the x-ray field during diagnostic use of the imaging system. SID is utilized to control the size of the x-ray beam in relation to the physical size of the x-ray image receptor to minimize the amount of non-diagnostic radiation that a patient may be subject to in the course of a diagnostic procedure. Further, certain regulatory standards specify that the SID must be clearly displayed to the operator or user of the system with a certain level of accuracy.

Generally, known installation and calibration procedures for establishing fixed SED setpoints and corresponding SID readouts require the presence of a field engineer who, through a trial and error process, calibrates the imaging system and installs fixed, preset detent positions that lock the x-ray source into various repeatable separation distances from the detector. For example, the field engineer may install an electromechanical switch, or other device, in the ceiling or the superstructure of the x-ray source that indicates to the user in a tactile or otherwise perceptible manner that the x-ray source is at one of the preset SID positions. Many radiographic imaging systems include industry-standard SID setpoints at separation distances of, for example, 40 inches, 60 inches, and 72 inches.

The installation and calibration procedure, however, becomes even more complex if the detector is non-stationary. In such event, the field engineer may repeat the setup and calibration procedure at multiple detector positions and install several setpoint or detent devices at the corresponding multiple determined SID positions.

Once the preset SID positions are determined and marked with a detent device, the SED positions are fixed. Thus, a user of the imaging system is not afforded flexibility in the event that the user may desire a SID position that is non-standard. Accordingly, even though either the x-ray source or the x-ray detector could be moved to a variety of different positions such that patients of various sizes could be accommodated or various anatomical parts could be more easily imaged, the actual positions in which the x-ray source could be located with respect to the x-ray detector are restricted to only those few positions which have corresponding fixed detent setpoints.

Conventional methods to calculate the source-to-image distance are unreliable and time consuming. These methods always required some parameter to be measured. Generally, operators conduct tests to calculate these parameters, and may encounter operator and calibration errors. Proposed solutions are adequate, however they themselves have certain drawbacks such as inaccurate measurements. These proposed solutions all require some known measured parameter to help guide the operators to calculate the source-to-image distance. Since the measurements supplied may be inaccurate, the data calculated can be unreliable and unsuitable for calibration purposes. Additionally, as mentioned above, the current techniques for calibrating a digital imaging systems are time consuming and error prone.

Thus, it would be desirable to provide a system and method for installing and calibrating a digital radiographic imaging system that would avoid time-consuming iterative procedures for determining fixed SID positions and for providing a calibrated readout and display of the actual SID. It would be further desirable if such a system and method would result in the elimination of, or reduced reliance on, fixed setpoints and physical fixed setpoint devices, thus affording greater flexibility and increasing the reliability of the system.

The present invention addresses one or more of the shortcomings noted above.

SUMMARY OF THE INVENTION

The present technique involves calculating the SID by utilizing a known relationship. For instance, the energy delivered from a uniform source to a surface normal to an area is proportional to the area, and inversely proportional to the square of the distance from the source to the surface of the area. Using this relationship, the SID is calculated by determining the intensity generated by two separate exposures. The SID for the two exposures are unknown and may be picked randomly, however the change in the distance from the first SID to the second SID is recorded. The technique provides that once the levels of intensity are measured for the same area, the SID may be calculated using the inverse square law as recited above. In another embodiment, the intensity levels of the generated exposures are held constant and a first and second times are measured with respect to the intensity levels. The measured times are then applied to the relationship governed by the inverse square law to determine the source to image distance.

DETAILED DESCRIPTION OF THE INVENTION

Figure 1:
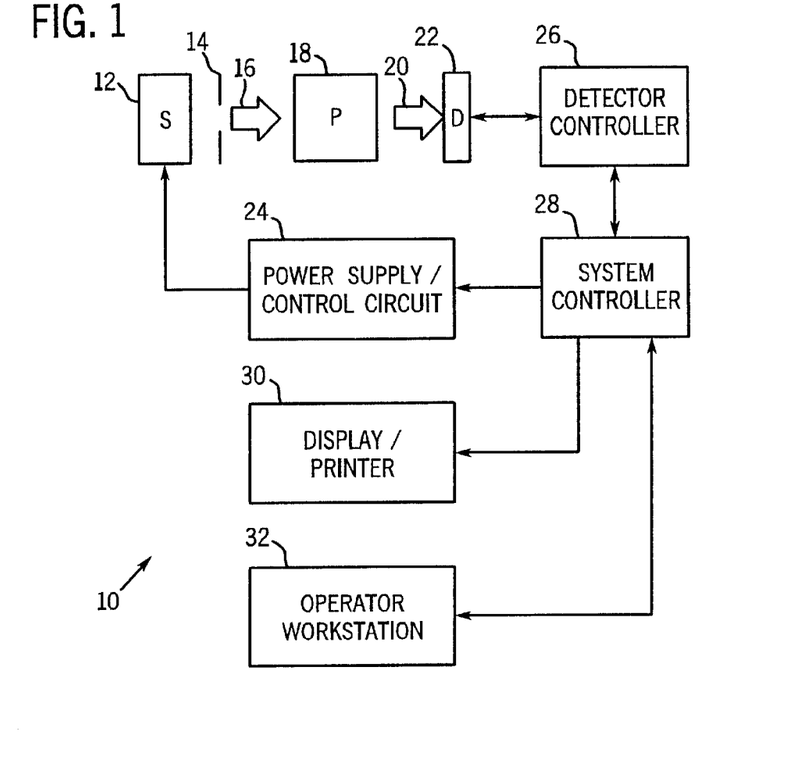
FIG. 1 is a diagrammatical overview of a digital x-ray imaging system in which the present technique is incorporated.

FIG. 1 illustrates diagrammatically an imaging system 10 for acquiring and processing discrete pixel image data. In the illustrated embodiment, system 10 is a digital x-ray system designed both to acquire original image data and to process the image data for display in accordance with the present technique. In the embodiment illustrated in FIG. 1, imaging system 10 includes a source of x-ray radiation 12 having a collimator 14. Source 12 is configured to generate an x-ray beam that passes through an opening in the collimator. Thus, collimator 14 permits a stream of radiation 16 to pass into a region in which a subject, such as a human patient 18 is positioned. A portion of the radiation 20 passes through or around the subject and impacts a digital x-ray detector, represented generally at reference numeral 22. As described more fully below, detector 22 converts the x-ray photons received on its surface to lower energy photons, and subsequently to electric signals, which are acquired and processed to reconstruct an image of the features within the subject.

It should be noted for the purposes of the present technique, the collimator 14 is positioned so that the radiation 20 received by the detector is detected in a particular area. Although, collimator 14 is illustrated in the present embodiment, it should be noted that the present technique does not require any knowledge of the type of collimator 14. Further, the present technique may be applied without the collimator 14. Thus, the collimator 14 is shown in the present embodiment only to provide a better understanding of the present technique. Also, in the embodiment illustrated in FIG. 1, imaging system 10 further includes a calculating circuit (not shown) to determine the distance from the source 12 to the detector or source to image distance (SID). The calculating circuit may record the intensity level of the exposure by sensing the level of exposure as well as being adapted to record time.

Source 12 is controlled by a power supply/control circuit 24 which furnishes both power and control signals for examination sequences. It should be noted that source 12 may be movable in longitudinal, lateral, and vertical directions, such that the source can be positioned to generate an x-ray field that may be detected by a detector 22 associated with a horizontal patient positioner or a detector 22 associated with a vertical positioner. Thus, the mobility of source 12 allows source 12 to be located at any number of positions such that an x-ray beam generated by source 12 can be centered with respect to detector 22 and such that the separation distance between source 12 and detector 22 can be varied.

As further illustrated in FIG. 1, detector 22 is coupled to a detector controller 26 which commands acquisition of the signals generated in the detector. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data. In the present context, system controller 28 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 28 is linked to at least one output device, such as a display or printer as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
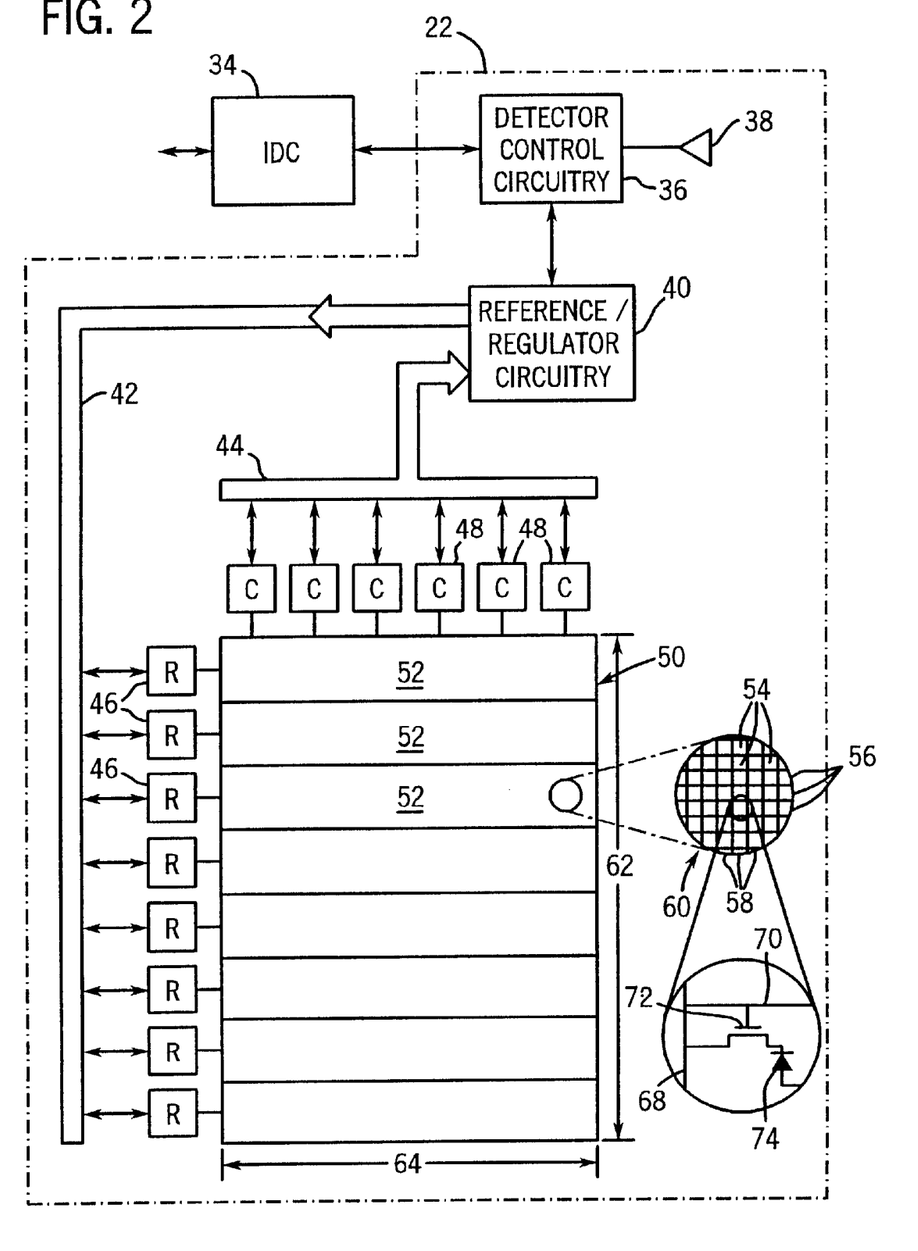
FIG. 2 is a diagrammatical representation of the functional circuitry for producing image data in a detector of the system of FIG. 1.

FIG. 2 is a diagrammatical representation of functional components of an exemplary digital detector 22. FIG. 2 also represents an imaging detector controller or IDC 34, which will typically be configured within detector controller 26. IDC 34 includes a CPU or digital signal processor, as well as memory circuits for commanding acquisition of sensed signals from the detector. IDC 34 is coupled via two-way fiberoptic conductors to detector control circuitry 36 within detector 22. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column drivers used to transmit signals during data acquisition phases of operation of the system. Circuitry 36 therefore transmits power and control signals to reference/regulator circuitry 40, and receives digital image pixel data from circuitry 40.

In a present embodiment illustrated, detector 22 consists of a scintillator that converts x-ray photons received on the detector surface during examinations to lower energy (light) photons. An array of photodetectors then converts the light photons to electrical signals which are representative of the number of photons or the intensity of radiation impacting individual pixel regions of the detector surface. Readout electronics convert the resulting analog signals to digital values that can be processed, stored, and displayed, such as in a display 30 or a workstation 32 following reconstruction of the image. In a present form, the array of photodetectors is formed on a single base of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics as described below. The drains of the transistors in a column are connected together and an electrode of each column is connected to readout electronics, as also described below.

In the particular embodiment illustrated in FIG. 2, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector.

In the illustrated embodiment, row drivers 46 and readout electronics 48 are coupled to a detector panel 50 which may be subdivided into a plurality of sections 52. Each section 52 is coupled to one of the row drivers 46, and includes a number of rows. Similarly, each column driver 48 is coupled to a series of columns. The photodiode and thin film transistor arrangement mentioned above thereby define a series of pixels or discrete picture elements 54 which are arranged in rows 56 and columns 58. The rows and columns define an image matrix 60, having a height 62 and a width 64, and a known number of rows and columns.

As also illustrated in FIG. 2, each pixel 54 is generally defined at a row and column crossing, at which a column electrode 68 crosses a row electrode 70. As mentioned above, a thin film transistor 72 is provided at each crossing location for each pixel, as is a photodiode 74. As each row is enabled by row drivers 46, signals from each photodiode may be accessed via readout electronics 48, and converted to digital signals for subsequent processing and image reconstruction.

Figure 3:
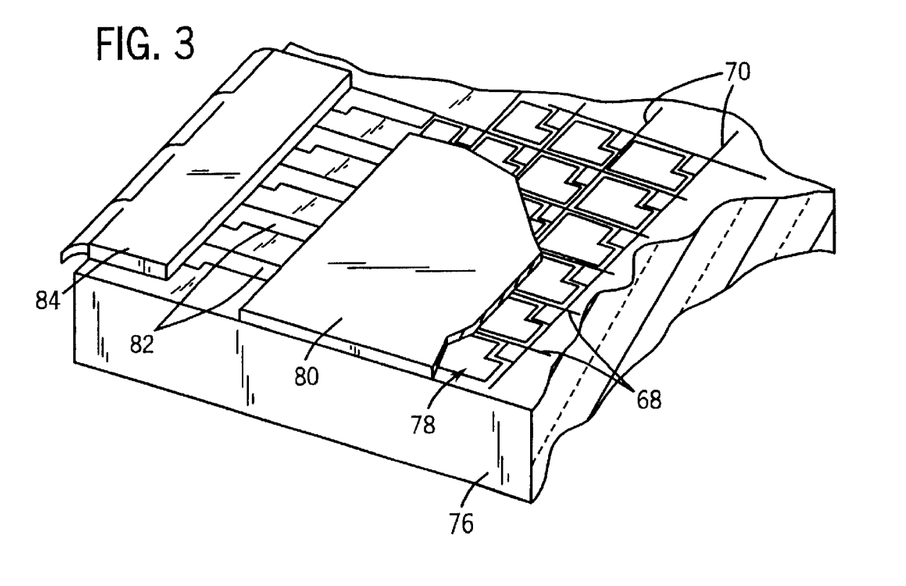
FIG. 3 is a side view of the image acquisition components of the system of FIG. 1, and, in particular, illustrates the orientation of a x-ray source with respect to a digital x-ray detector associated with a patient positioner.

FIG. 3 generally represents an exemplary physical arrangement of the components illustrated diagrammatically in FIG. 2. As shown in FIG. 3, the detector may include a glass substrate 76 on which the components described below are disposed. Column electrodes 68 and row electrodes 70 are provided on the substrate and an amorphous silicon flat panel array 78 is defined, including the thin film transistors and photodiodes described above. A scintillator 80 is provided over the amorphous silicon array 78 for receiving radiation during examination sequences as described above. Contact fingers 82 are formed for communicating signals to and from the column and row electrodes, and contact leads 84 are provided for communicating the signals between the contact fingers and external circuitry.

Before imaging system 10 may be used to perform examination sequences, system 10 is properly installed and calibrated to ensure compliance with customer needs, performance requirements, and various regulatory standards. Accurate establishment and calculation of the SID assists in appropriate control of the size of the x-ray field generated during diagnostic use of system 10. It should be noted that the setup of SID involving the establishment of SID setpoints is undesirable with respect to the present technique for calculating the SID accurately.

Figure 4:
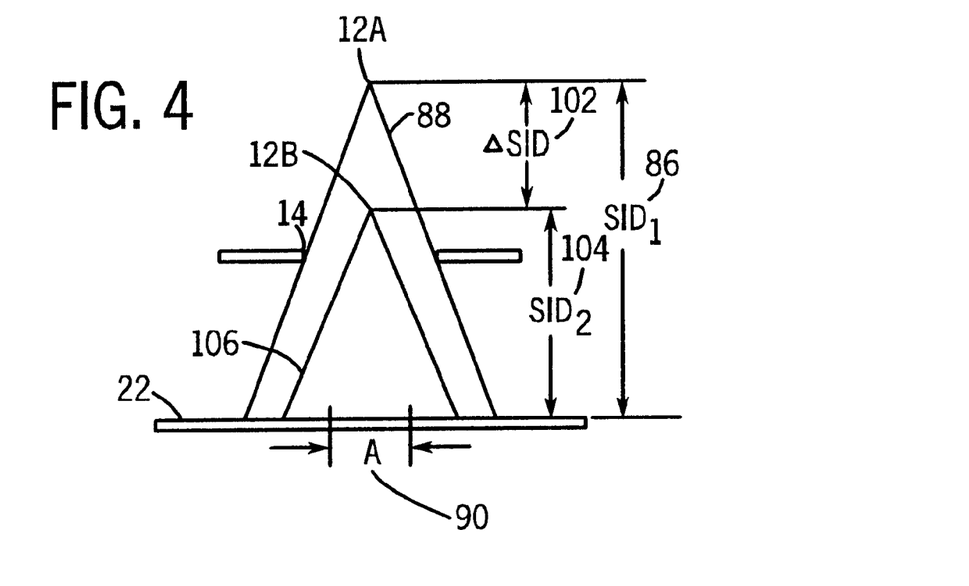
FIG. 4 illustrates an exemplary installation and calibration technique for the digital x-ray imaging system of FIG. 1, in which the x-ray source generates an x-ray beam having a fixed angle while the source is at two different separation distances from the detector.
Figure 5:
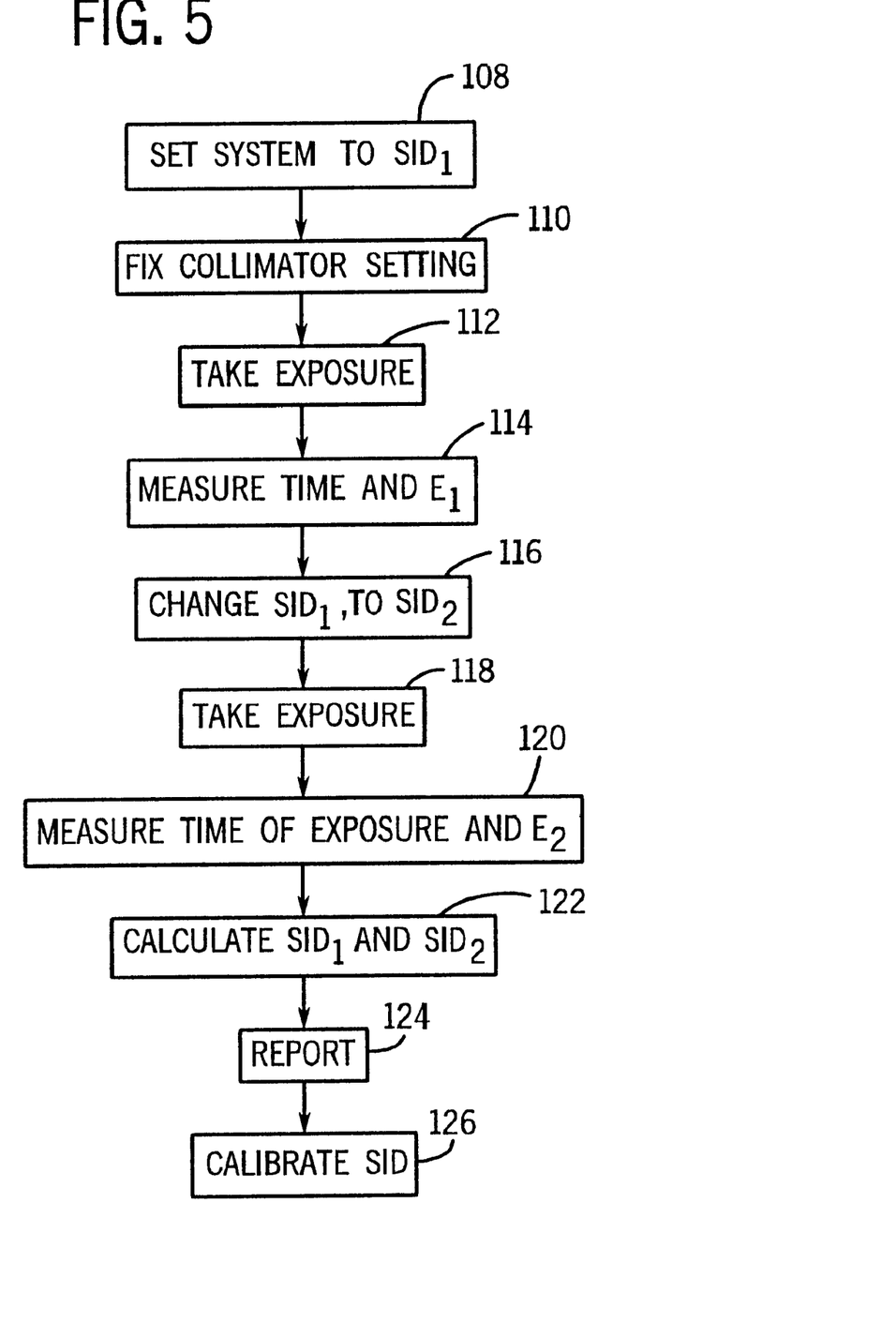
FIG. 5 illustrates a flowchart representing the steps in the present technique for determining the source to image distance in an exemplary imaging system.

Exemplary techniques for establishing SID and providing a calibrated SID readout may be understood with reference to FIGS. 4 and 5. Turning first to FIG. 4, x-ray source 12 is shown, which is generally mounted to a movable support structure (not shown) and positioned with respect to detector 22 which is associated with a patient positioner (not shown). Although the detector 22 is illustrated in a horizontal orientation, it should be understood that detector 22 may be positioned either horizontally or vertically depending on the type of exposure needed from the patient. The technique illustrated in FIG. 4 involves generating an x-ray beam at two different source positions and detection of the respective x-ray beams at the detector.

As further illustrated in FIG. 4, source 12 is at a first position 12A and generates a first x-ray beam 88 that is detected by the detector 22. The size of the x-ray beam 88 is determined by the size of the opening in the collimator 14. The beam 88 impacts the detector upon an area 90, which is connected to a calculating circuit (not shown) which may be utilized to measure the intensity of the beam 88 and other parameters. The distance between the first source position 12A and the detector 22 corresponds to a first SID1 and referenced generally by the numeral 86. Thus, the source to image distance SID1 is the distance between the detector 22 and a focal spot of an x-ray beam 88 generated by source 12 while at the first source position 12A.

Figure 4A:
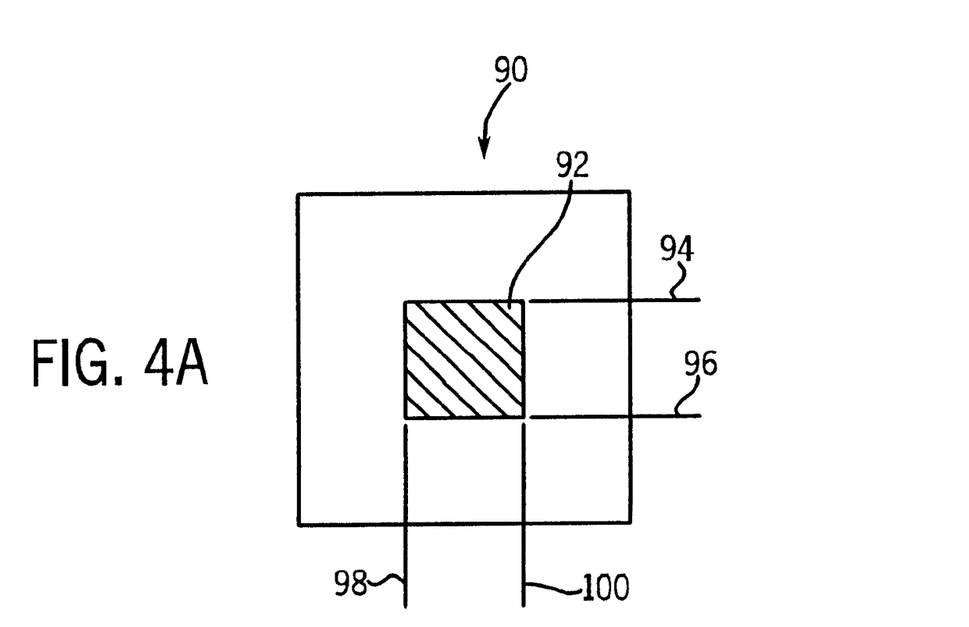
FIG. 4a illustrates in further detail an element represented in FIG. 4, specifically, the area where the x-ray beam is detected in a exemplary radiographic digital detector.

X-ray beam 88 impacts the detector 22 at an impact area 90, which is illustrated by FIG. 4a. Although impact area 90 is illustrated as having a rectangular or square shape, it should be understood the impact area 90 may be curved such that the periphery of impact area 90 is circular or otherwise curvilinear. In the present technique, the area 92 within the larger detected area 90 is utilized in sensing the intensity level. For instance, row line 94 to row line 96 and column lines 98 and 100 may be selected for the specific area to be analyzed. Although, in this embodiment the area 92 is selected as such, it should be noted that a larger or smaller area may be selected and the area 92 given is only provided as an example. Thus, detector controller 26 and system controller 28 may determine the size of the impact area 90 and more importantly the area 92 where the intensity levels for the exposures are measured.

Turning back to FIG. 4, a second exposure is also illustrated. For this exposure, the source 12 is moved to a second source position 12B. The change in the distance from the first source position 12A to the second source position 12B is referenced as $\Delta SID$ and by reference numeral 102. SID2, as indicated by reference numeral 104, is the distance between detector 22 and a focal spot of an x-ray generated by source 12 while at source position 12B. Thus, a second x-ray beam 106 is generated by source 12 at position 12B and impacts the detector 22. It should be noted that the size of the opening of the collimator 14 remains the same with respect to the first and second exposures. The collimator 14 opening may be changed from the first exposure to the second exposure, however there is conveniently some common area 92 detected from the first and second exposures. Furthermore, it should be understood that the distance between the first source position 12A and the second source position 12B referenced by $\Delta SID$ 102 is a known quantity, (i.e. distance) whereas SID1 86 and SID2 104 remain unknown or uncalibrated quantities that may be calculated by the present technique.

FIG. 5 illustrates a flowchart representing a method for calculating the SID utilizing the technique illustrated in FIG. 4 and 4a. As will be appreciated by those skilled in the art, the energy delivered from a uniform source to a surface normal to the source, of an area A, is proportional to the area A, and inversely proportional to the square of the distance from the source to the surface of the area A. In the present technique it is suitable to make two exposures as illustrated in FIG. 4 to calculate the SID utilizing the inverse square relationship. Initially, as indicated by step 108, the imaging system is set to a random SID value for the first exposure, as referenced by SID1 in FIG. 4. The collimator 14 is calibrated accordingly to detect the exposure at a selected area 90 on the detector panel as indicated by step 110. As mentioned above, the collimator 14 is set so that the detector may be adapted to detect the x-ray beam in a specified area 92 in the first and second exposures. In step 112, a first exposure is taken and the detector detects the exposure on the selected area 90. The intensity E1 of the exposure is measured using the selected area 92 of the digital detector as indicated by step 114. It should be mentioned that the intensity E1 is related to the first source-to-image distance SID1 according to the following relationship:

$$E1=(k*A)/(SID1)^2;$$

where E1 represents the intensity of the exposure, k represents an unknown constant, A represents the area, and SID1 represents the distance from the source position 12A to the image. It should be noted that the time of the exposure may be monitored and utilized to calculate the SID rather than using the intensity of the exposure.

Next, the source 12 is moved to different position 12B as indicated by step 116, and the change in SID is indicated by ΔSID. As mentioned above, the source-to-image distance after the source position is moved, is referenced by SID2. Thus, for the second exposure as indicated by step 118, the source 12 is moved some known distance ΔSID and an essentially identical exposure is executed from the source position 12B. The intensity E2 of the second exposure is measured as indicated by step 120.

Once the measurements are recorded the SID values may be calculated as indicated by step 122. The intensity E2 of the second exposure is related to SID1 or the first source-to-image distance by the following relationship:

$$E2=k*A/(SID1+\Delta SID)^2;$$

where E2 represents the intensity of the second exposure, k represents the unknown constant, SID1 represents the first source to image distance, and ΔSID represents the distance from the first source position 12A to the second source position 12B. Combining the above mentioned equations and solving the resulting quadratic, and rejecting the negative root, the following relationship is derived:

$$SID1=\Delta SID(E2+(E1*E2)^0.5)/(E1-E2).$$

Thus, using this relationship the SID1 value may be calculated by inputting the change in source-to-image distance ΔSID and the respective measured intensity levels E1 and E2. It should be understood that once the SID1 is determined, the SID2 value can be determined by either adding or subtracting the change in the distance ΔSID. Once the SID1 and SID2 values are calculated and reported as indicated by steps 124 and 126, the x-ray imaging system may be calibrated accordingly.

In an alternative embodiment, the time T may be utilized to calculate the source-to-image distance. In this embodiment, the source 12 generates an x-ray beam 88 that makes a first exposure on the detector 22. The elapsed time T1 for the first exposure is measured. The source 12 is then moved to source position 12B from source position 12A. A second x-ray beam 106 from source position 12B is detected by the detector 22. The second exposure is continued until the total intensity of the second exposure equals the intensity of the first exposure. The time T2 that the intensity E2 of the second exposure takes to equal the intensity of the first exposure E1 is measured. Thus, the following relationship is made regarding the first intensity E1 with respect to time, area and SID1:

$$E1=(K*A*T1)/(SID1)^2.$$

Similarly, after the second exposure, the relationship with respect to the time, area, SID1 and the change in source to image distance ΔSID can be indicated by:

$$E1=(K*A*T2)/(SID1+\Delta SID)^2.$$

It should be noted that k is a different unknown constant than in the previous embodiment. Further, once the equations are combined, the following relationship can be derived:

$$SID1=\Delta SID(T1+((T1*T2)^0.5))/(T2-T1).$$

Thus, the time may be measured and inputted within the equation as well as the change in the source-to-image distance ΔSID, providing the first source-to-image distance SID1 and allowing the operator to calibrate the radiographic imaging system accordingly.

It should be noted that this approach conveniently makes use of the ability to measure the exposure time, and has the advantage that it may be implemented on a conventional film-based system which uses an ion chamber for exposure control. In the specific embodiment where an ion chamber may be used, the exposed area can be held constant using an aperture fixed in front of the ion chamber.

It should also be mentioned that slightly different algorithms may be used which have neither constant exposure time or constant intensity levels. In such embodiments, the SID may be computed by measuring the change in intensity level as a result of changing the SID and using the inverse square relationship to determine the SID. As mentioned above, the inverse square relationship refers to the proportionality energy delivered from a uniform source to a surface normal to the area, and the inverse proportionality to the square of the distance from the source to the surface of the area.

Further, the inverse square law provides an excellent basis for calibration for a true point source of uniform intensity, and with a receptor surface which is a portion of a sphere centered on the point source. However, the error introduced by the flat detector surface and by the non-ideal focal spot source is quite small, particularly when the area of the detector used for the measurement is properly chosen, as when it represents a small solid angle from the focal spot. In an alternative embodiment, it is possible to use a larger angle, and introduce calculations which correct this effect.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for determining a distance between a x-ray source and a digital x-ray detector positioned to detect a x-ray beam generated by the x-ray source, the method comprising the acts of:

positioning an imaging system having a first source-to-detector position, the detector having an area for receiving a first x-ray beam;

generating a first exposure with the system being positioned at the first source-to-detector position for a first duration of time;

measuring a first intensity level for the first x-ray beam detected by the detector;

resetting the imaging system to a second source-to-detector position, the detector having an area for receiving a second x-ray beam;

generating a second exposure with the system being positioned at the second source-to-detector position for a second duration of time;

measuring a second intensity level for the second x-ray beam detected by the detector; and calculating the distance from the x-ray source to the digital detector based upon the first and second exposures and the first and second positions.

2. The method as in claim 1, wherein the digital detector comprises a plurality of rows and columns of pixels which define an image matrix, and the first and second intensity levels are measured on a same area as defined by known rows and columns of pixels.

3. The method as in claim 1, wherein the act of resetting the imaging system comprises the act of recording the difference in the distance from the first position to the second position.

4. The method as in claim 3, wherein the act of calculating the distance from the x-ray source to the digital x-ray detector comprises the act of determining the distance from the x-ray source to the digital x-ray detector utilizing the relationship $SID1=\Delta SID\ (E2+((E1*E2)^{0.5}))/(E1-E2)$, where SID1 represents the distance from the source to the detector in the first position, $\Delta SID$ represents difference in the source-to-detector distances between the first position and the second position, and E1 and E2 represent the first and second intensities, respectively.

5. The method as in claim 1, wherein the act of measuring comprises an act of recording the first duration of time and the second duration of time for the first and second exposures, the second duration of time being equal to the time for the second intensity level to equal the first intensity level.

6. The method as in claim 5, wherein the act of calculating the distance from the x-ray source to the digital detector comprises the act of determining the distance from the first position to the detector utilizing the relationship $SID1=\Delta SID\ (T2+(T1*T2)^{0.5}))/(T2-T1)$, SID1 represents the distance from the source to the detector in the first position, $\Delta SID$ represents difference in the source-to-detector distances between position and the second source position, and T1 and T2 represent the first and second durations of time, respectively.

7. A digital radiographic imaging system, comprising:
a digital x-ray detector;
a x-ray source configured to generate an x-ray beam, the x-ray source being displaced from the detector and configured to generate a first exposure producing a first x-ray beam having a first impact area when detected at the detector and a second exposure producing a second x-ray beam having a second impact area when detected at the detector, the first exposure adapted to be generated from the source at a first source-to-detector position and the second exposure adapted to be generated from the source at a second source-to-detector position; and
a calculating circuit configured to determine a source-to-image distance between the source and the detector based on first and second intensity levels detected on an area and the change in the source-to-detector position from the first x-ray beam detected by the detector to the second x-ray beam detected by the detector.

8. The system as in claim 7, wherein the first and second impact areas are equal.

9. The system as in claim 7, wherein the digital detector comprises a plurality of rows and columns of pixels defining an image matrix, and the first intensity level is determined by detecting a pair of rows and columns of pixels corresponding to the peripheral edges of the impact area, and the second intensity level is determined by detecting a pair of rows and columns of pixels corresponding to peripheral edges of the impact area.

10. The system as in claim 7, wherein the calculating circuit is configured to determine the source-to-image distance calculated by the relationship $SID1=\Delta SID(E2+((E1*E2)^{0.5}))/(E1-E2)$, where SID1 represents the distance from the source to the detector in the first source-to-detector position, $\Delta SID$ represents the change in the distance from the source to the detector from the first source-to-detector position to the second source position, and E1 and E2 represent the first and second intensities of the first and second exposures, respectively.

11. The system as in claim 7, wherein first and second durations of time for the first and second exposures are recorded, the first and second durations of time being related to the first and second intensity levels.

12. The system as in claim 11, wherein the second duration of time is measured with respect to the second intensity level equaling the first intensity level.

13. The system as in claim 7, wherein the calculating circuit is configured to determine the first source-to-image distance calculated by the relationship $SID1=\Delta SID(T2+((T1*T2)^{0.5}))/(T2-T1)$, where SID1 represents the distance from the source to the detector in the first position, $\Delta SID$ represents the change in the distance from the source to the detector, from the first position to the second position, and T1 and T2 represent the first and second durations of time for the first and second exposures, respectively.

14. A method for determining a distance between a x-ray source and a digital x-ray detector positioned to detect a x-ray beam generated by the x-ray source, the method comprising the acts of:
positioning an imaging system having a first source position;
generating a first exposure for a first duration of time with the source being positioned at the first source position;
measuring a first intensity level and the first duration of time for the first exposure;
resetting the imaging system to a second source position;
generating a second exposure for a second duration of time with the source being positioned at the second source position;
measuring a second intensity level equal the first intensity level and the second duration of time for the second exposure; and
calculating the distance from x-ray source to the digital detector.

15. The method as in claim 14, wherein the second duration of time is the time required for the second intensity level to equal the first intensity level.

16. The method as in claim 14, wherein the act of resetting the imaging system comprises the act of recording the difference from the first source position to the second source position.

17. The method as in claim 16, wherein the act of calculating the distance from the x-ray source to the digital x-ray detector comprises the act of determining the distance from the x-ray source to the digital x-ray detector utilizing the relationship $SID1=\Delta SID(T1+((T1*T2)^{0.5}))/(T2-T1)$, where SID1 represents the distance from the source to the detector the first source position, $\Delta SID$ represents the difference in the distances from the source to the detector between the first source position to the second source position, and T1 and T2 represent the first and second durations of time for the first and second exposure, respectively.

18. A system for determining a distance between a x-ray source and a digital x-ray detector positioned to detect a x-ray beam generated by the x-ray source, comprising:
means for positioning an imaging system at a first source-to-detector position;

means for generating a first exposure with the system positioned at the first source-to-detector position;

means for measuring a first intensity level for the first exposure;

means for resetting the imaging system to a second source-to-detector position;

means for generating a second exposure with the system positioned at the second source-to-detector position;

means for measuring a second intensity level for the exposure; and means for calculating the distance from x-ray source to the digital detector based upon the first and second exposures and the first and second positions.

19. The system as in claim 18, wherein the digital detector comprises a plurality of rows and columns of pixels which define an image matrix, and the means for measuring the first and second intensity levels determine the intensity levels for a same area as defined by known rows and columns of pixels.

20. The system as in claim 18, wherein the means for resetting the imaging system comprises means for recording the difference in the distance between the source and the detector from the first position to the second position.

21. The system as in claim 18, wherein the means for calculating the distance from the x-ray source to the digital x-ray detector comprises the means for determining the distance from the x-ray source to the digital x-ray detector for the first exposure utilizing the relationship $SID1=\Delta SID (E2+((E1*E2)^{0.5}))/(E1-E2)$, SID1 represents the distance between the source and the detector in the first position to the detector, $\Delta SID$ represents the difference in the distances from the first position to the second position, and E1 and E2 represent the first and second intensities, respectively.

22. The system as in claim 18, comprising means for detecting a first duration of time of the first exposure and a second duration time of the second exposure, the second duration of time measured to when the intensity level of the first exposure equals the second intensity level of the second exposure.

23. The system as in claim 22, wherein the means for generating the second exposure generates the second exposure for the second duration of time such that the second intensity level equals the first intensity level.

24. The system as in claim 23, wherein means for calculating the distance comprises means for determining the distance from the x-ray source to the digital x-ray detector for the first exposure utilizing the relationship: $SID1=\Delta SID (T1+((T1*T2)^{0.5}))/(T2-T1)$, where SID1 represents the distance from the source to the detector from the first position, $\Delta SID$ represents the difference in the distance from the first to the second positions, and T1 and T2 represent the first and second durations of time, respectively.

* * * * *